(12) United States Patent
Golz-Berner et al.

(10) Patent No.: US 6,623,725 B2
(45) Date of Patent: Sep. 23, 2003

(54) COSMETIC COMPACT OR CREME POWDER

(75) Inventors: Karin Golz-Berner, Monaco (DE); Leonhard Zastrow, Monaco (DE)

(73) Assignee: Coty B.V. (NL)

( * ) Notice: Subject to any disclaimer, the term of this patent is extended or adjusted under 35 U.S.C. 154(b) by 0 days.

(21) Appl. No.: 10/239,494

(22) PCT Filed: Mar. 8, 2001

(86) PCT No.: PCT/DE00/00953
§ 371 (c)(1),
(2), (4) Date: Sep. 20, 2002

(87) PCT Pub. No.: WO01/70186
PCT Pub. Date: Sep. 27, 2001

(65) Prior Publication Data
US 2003/0082119 A1 May 1, 2003

(30) Foreign Application Priority Data
Mar. 23, 2000 (DE) .......................... 100 15 363

(51) Int. Cl.$^7$ .............................. A61K 7/42; A61K 7/44; A61K 7/00; A61K 35/78
(52) U.S. Cl. .......................... 424/59; 424/60; 424/400; 424/401; 424/725; 424/778
(58) Field of Search ........................ 424/59, 60, 400, 424/401, 725, 778

(56) References Cited

U.S. PATENT DOCUMENTS 5,559,146 A * 9/1996 Sablon et al. ............... 514/468

* cited by examiner

Primary Examiner—Shelley A. Dodson
(74) Attorney, Agent, or Firm—Pendorf & Cutliff

(57) ABSTRACT

The invention relates to a cosmetic compact or cream powder which is provided with self-tanning agent and optionally light-protecting characteristics. The dihydroxy acetone (DHA) portion of said powder is fully used for coloration. The cosmetic powder contains a self-tanning agent selected from mixtures of DHA and aqueous mahakanni extract and mixtures of DHA with mahakanni and tulips extract, additional chromophore pigments, a wax or a mixture of several waxes, a powder basis and optionally additional cosmetic auxiliaries and active agents in stable homogeneous distribution. The inventive powder is produced by mixing the powder basis and a first portion of the pigments with the molten wax. The self-tanning agent and a second portion of the pigments in an aqueous-alcoholic suspension having a pH value ranging from 3–4 are subsequently added into the molten was mixture at 65 to 70° C. The entire mixture is steered, homogenised and cooled.

10 Claims, No Drawings

COSMETIC COMPACT OR CREME POWDER

CROSS REFERENCE TO RELATED APPLICATION

This application is a national stage of PCT/DE01/00953 filed Mar. 8, 2001 and based upon DE 100 15 363.1 filed Mar. 23, 2000 under the International Convention.

BACKGROUND OF THE INVENTION

1. Field of the Invention

The invention relates to a cosmetic compact or cream powder which has self-tanning and optionally light-protecting characteristics.

2. Description of the Related Art

It is known to produce dihydroxy acetone (DHA) based self-tanners in the form of various liquid emulsions or gels. In many cases however, further additives are necessary in order to stabilize these products. For example, EP-B-752842 describes a DHA composition which contains certain sulphite salts and optionally amino acids. According to WO96/31190, DHA is combined with lecithins and optionally sterols and then heated in an aqueous solution and encapsulated in liposomes in order to obtain a stable product.

In regard to the manufacture of pressed powders or cream powders, there is the problem that these normally contain wax portions which have to be heated up to 60–85° C. in order to enable the other ingredients of the formulation to be added. However, DHA increasingly tends to partially react with other constituents at these high temperatures so that the tanning capacity of the product is lost to a varying degree. Therefore, hardly any such powders have been manufactured to date and there are no such products available on the market.

SUMMARY OF THE INVENTION

The object of the invention is to provide compact or cream powders which have a very good coloration effect based on self-tanning agents which are distributed in a stable, homogeneous manner and in which the dihydroxy acetone portion is fully used for coloration.

According to the invention, the cosmetic compact or cream powder consists of a self-tanning agent selected from among mixtures of dihydroxy acetone (DHA) and mahakanni (*Eclipta alba* Hassk) extract and mixtures of DHA, mahakanni extract and tulips extract, additional chromophore pigments, a wax or a mixture of several waxes, a powder base and optionally additional cosmetic auxiliaries and active agents in stable homogeneous distribution, the mahakanni extract being an aqueous extract containing 2-hydroxy-1,4-naphthochinon and eumelanin and the tulips extract being an aqueous extract from tulips exposed to UV radiation containing thymine and pyrimidine dimers and mixtures thereof.

The use of a mixture of DHA and mahakanni is particularly advantageous. mahakanni is a natural tanning colour obtained from the mahakanni plant (*Eclipta alba* Hassk) which substantially consists of 2-hydroxy-1,4-naphthochinon and Eumelanin and which brings about a particularly natural brown skin colour. The exact Latin name is *Eclipta alba* Hassk (Syn) *Eclipta prostata*.

The self-tanning effect can be increased by adding a tulips extract (Tulipa; from garden tulips and wild tulips, particularly DNA-rich tulip species). The said extract has high contents of dimers and nucleotides and is produced and marketed by Greentech, St. Beauzire, France under the name TULIPA NUCLEOTIDS. The extract has high contents in the range of 8–40% by weight of thymine and/or pyrimidine dimers and brings about a clear pigmentation effect when applied on to the skin.

Preferably, 2-hydroxy-1,4-naphthochinon is contained in the range of 37–42% by weight and Eumelanin is contained in the range of 47–52% by weight relative to the total content of the constituents contained in the mahakanni extract.

The mahakanni extract further contains ascorbic acid, lecithins, shpingomyelin, β-carotene and phosphosphingolipid in an overall concentration ranging from 7 to 10% by weight relative to the total weight of the extract.

The mahakanni extract, which is preferably encapsulated in liposomes, can be used in concentrations ranging from 0.5 to 10% by weight relative to the total weight of the powder. The extract has a refractive index of 1.4–1.5 and does not contain any isoflavonoids.

The tulips extract, which can also be encapsulated in liposomes, is added into the powder in concentrations ranging from 0.5 to 10% by weight relative to the total weight of the powder.

The DHA concentration is in the range of 0.1–5% by weight relative to the total weight of the powder.

The powder according to the invention can further contain a sunscreen in the form of a UV filter.

The invention enables substantially the whole portion of the self-tanning agent to be effective within the formulation and to avoid or considerably delay losses or side reactions of the DHA. In particular, a correct pH value of the premix, i.e. a mixture made up of part of the pigments, DHA and optionally the sunscreen, considerably contributes to that the mixture can be added in a problem-free manner and a stable formulation is obtained. The pH value can be influenced as necessary by adding known, cosmetically acceptable pH adjusters such as EDTA, acetic acid, citric acid, etc.

By avoiding reaction-induced losses, the content of chromophore constituents, particularly DHA, can be adjusted much more precisely, not to say it becomes possible for the first time to almost exactly adjust the concentration of the said constituents.

The overall content of self-tanning agents is in the range of 1–15% by weight relative to the entire composition, the mixture containing max. 5% by weight of DHA, 10% by weight of mahakanni extract and 10% by weight of tulips Extract. There are no restrictions as regards the miscibility of mahakanni extract and tulips extract with one another and the respective quantities are determined in accordance with the tanning effect desired. The same is true of the miscibility of the two extracts with DHA.

Substances which can be selected as pigments, pigment mixtures or powders having a pigment-like effect, including such ones which have a gloss effect, include e.g. iron oxides, natural aluminium silicates such as Ochre, Titanium Dioxide, Zinc Oxide, Silica, Mica, Kaolin, clays containing manganese such as Umber and Red Bole, Calcium Carbonate, Talc, Mica-Titanium Oxide, Mica-Titanium Oxide-Iron Oxide, Bismuth Oxychloride, nylon globules, ceramic globules, expanded and non-expanded synthetic polymer powders, powdery natural organic compounds such as ground solid algae, ground parts of plants, encapsulated and non-encapsulated cereal starches and mica-titanium oxide-organic colour.

For the aqueous-alcoholic pigment solution or suspension, monovalent alcohols are used, e.g. ethanol, iso-propanol, n-propanol or mixtures thereof. Polyvalent alcohols can also be used, e.g. glycerine, a propane diol or a butane diol, advantageously also a mixture of two or more thereof.

The alcohol concentration is in the range of 1–10% by volume relative to the pigment solution or suspension.

Preferably, Octyl Methoxycinnamate is used as organic sunscreen (filter). Other suitable filters are Benzophenone-3, Butyl Methoxybenzoylmethane or 4-Methylbenzylidene Camphor or mixtures thereof. The concentration of the said filters can be in the range of 1–10% by weight relative to the total weight of the powder. It has been found that DHA is stabilized very well if DHA and a sunscreen of the aforesaid types are present at the same time.

In addition to the alcohol-soluble organic sun filter, a water-soluble organic sun filter can be contained. These include e.g. Benzophenone-3 and Phenylbenzimidazole Sulfonic Acid. The concentration of these water-soluble filters can be in the range of 2–15% by weight.

The powder according to the invention can have a Sun Protection Factor of 5 to 15 provided it contains the corresponding sun filters.

The powder according to the invention can contain further cosmetic active agents, e.g. antioxidants or scavengers, preservatives, moisturizing substances, fragrance, polar and non-polar oils, polymers, copolymers, emulsifiers, stabilizers, plant-based active agents, polymers, anti-inflammatory natural active agents.

Antioxidants include vitamins, such as Vitamin C and derivatives thereof, e.g. ascorbyl acetate, ascorbyl phosphate and ascorbyl palmitate; Vitamin A and derivatives thereof; folic acid and derivatives thereof, Vitamin E and derivatives thereof, such as tocopheryl acetate; flavons or flavonoids; amino acids, such as histidine, glycine, tyrosine, tryptophan, and derivatives thereof; carotenoids and carotenes, such as α-Carotene, β-Carotene; uric acid and derivatives thereof, α-hydroxy acids, such as citric acid, lactic acid, malic acid; stilbene and derivatives thereof, etc.

A particular advantageous mixture of enzymes and vitamins is a decomposition product obtained by ultrasonic decomposition of a yeast, the decomposition product containing Superoxiddismutase (SOD), Protease, Vitamin $B_2$, Vitamin $B_6$, Vitamin $B_{12}$, Vitamin $D_2$ and Vitamin E. Preferably, the said decomposition product contains at least 150 U/ml of SOD, protease and Vitamins B and D, the ratio of SOD to protease in international units being in the range of at least 3:1 to 8:1.

It is particularly advantageous that the enzyme/vitamin mixture be produced by means of an ultrasonic decomposition process which is described in DE 4241154C1 and in which a cell dispersion or suspension is passed through an ultrasonic exposure area in an ultrasonic flow-through cell, the sonotrode extending into the flow-through cell up to half or two thirds of its length and being immersed in the medium to be exposed to ultrasound. The sonsotrode has an angle of 80.5 to 88.50°, related to the entrance surface of the sonotrode, and the ratio of the sonotrode's immersed length in mm to the volume exposed to ultrasound in ml is adjusted to a value of 1:1.1 to 1:20. The portion of solid matter contained in the medium to be exposed to ultrasound is in the range of 1:0.02 to 1:2.2 (in % by weight).

Yeasts, such as baker's yeast, brewer's yeast, wine yeast as well as specially treated yeasts, such as yeasts enriched with SOD, can be used as cell dispersion. A preferred cell dispersion contains e.g. *Saccharomyces cerevisiae*.

Advantageously, a further active agent contained in the preparation can be kaolin according to WO96/17588, which kaolin has been modified with spherical $TiO_2$ or $SiO_2$ particles the particle size of which is <5 μm, the said spherical particles making up 0.5 to 10% by weight of the kaolin mixture. In this way, the preparation feels very soft on the skin and has an additional anti-inflammatory effect.

The modified kaolin can be contained in the range of 0.1–6% by weight relative to the total weight of the preparation.

The oils used for the invention can be common cosmetic oils, such as a mineral oil; Hydrogenated Polyisobutene; Squalane produced synthetically or made from natural products (INCI name: Squalane, e.g. Synthesqual®, Cosbiol®) ; cosmetic esters or ethers wich can be branched or linear, saturated or unsaturated; vegetable oils; or mixtures of two or more thereof.

Depending upon the oils used, the cosmetic characteristics of the solid composition, such as degree of transparency, softness, hardness, spreading effect, are influenced. Thick oils are preferred.

Waxes which can be used in the powder according to the invention are natural plant-based waxes, animal waxes, natural and synthetic mineral waxes and synthetic waxes. These include e.g. Carnauba Wax, Candelilla Wax, Beeswax, Wool Wax, Paraffin, Ceresin, Ozokerite, Silicone, polyethylene glycol waxes or polyethylene glycol ester waxes.

Powder bases are substantially round solid particles the particle size of which is approximately 25–110 μm and include e.g. silicates such as Kaolin, Aerosil, Talc; carbonates such as magnesium carbonate, calcium carbonate; oxides such as zinc oxide, titanium oxide; stearates such as zinc stearate, magnesium stearate, aluminium stearate; starch; protein decomposition products such as pulverized silk; labilin; synthetic organic polymerisation products; zinc decanate or magnesium decanate.

The water content of the creams according to the invention does not exceed 15% by weight, preferably it is below 12% by weight.

The invention also relates to a method for manufacturing the said compact or cream powder by mixing the powder base and optionally additional cosmetic auxiliaries and active agents and a first portion of 90–50% by weight of the chromophore pigments with the molten wax or wax mixture, subsequently adding the self-tanning agent selected from among mixtures of dihydroxy acetone (DHA) and mahakanni extract and mixtures of DHA, mahakanni extract and tulips extract, adding a second portion of 10–50% by weight of the pigments in an aqueous-alcoholic suspension having a pH value ranging from 3 to 4 into the molten wax mixture at a temperature of 65 to 70° C., stirring the entire mixture until it is homogeneous and cooling the mixture while maintaining its homogeneity.

It is particularly critical that the pH value be correct when the suspension is added.

Preferably, the mixture is cooled while stirring moderately and at a constant cooling rate of 1–2° C./min in order to avoid crystallization of the wax and maintain a homogeneous mixture.

The invention will hereinafter be explained in detail by way of examples. All quantities are in % by weight if not indicated otherwise.

EXAMPLE 1

Self-tanning Cream Powder I

| | |
|---|---|
| Ceraflex 3547 | 1.5 |
| Ozokerite Wax SP 1020 | 2 |
| Candelilla Wax Substitute | 3 |
| Synchrowax HGLC | 2.3 |
| Acide B glycerrhetinique | 0.01 |
| Nipasol M | 0.2 |
| Nipagine M | 0.4 |
| α-Tocopherol Acetate | 0.5 |
| Cosmacol EOI | 10 |
| $TiO_2$ | 5 |
| Iron Oxide Red 7054 | 0.4 |
| ZnO | 4 |
| Cogilor Ochre 90076 | 1.5 |
| Black 1557 | 0.14 |
| $SiO_2$ | 4 |
| Crodamol Osu | 6 |
| Modified* Kaolin | 2.5 |
| Orgasol 20002 Extd Nat Cos | 2 |
| Boron Nitride CCS102 | 2 |
| Dryflo Plus | 10 |
| Talc | q.s. ad 100 |
| Silicone Oil | 6 |
| Mahakanni Extract STLC+ | 2.5 |
| DHA | 2.5 |
| Octyl Methoxycinnamate | 1.0 |
| Parfum | 0.5 |
| Water | 12 |
| Biophilic H | 3 |
| Citric Acid | q.s. |

*according to WO96/17588
+Campo Research & Development Systems, Singapore

Processing

A solid mixture of the pigments $TiO_2$, ZnO, Iron Oxide, $SiO_2$, black and ochre was prepared by slightly mixing the aforesaid ingredients and divided into two batches of 65% by weight (pigment batch 1) and 35% by weight (pigment batch 2).

Pigment batch 1, the sun filter (here: Octyl Methoxycinnamate), the antioxidant and the parfum were added into a 3.5 vol.-% aqueous-alcoholic solution containing DHA and Mahakanni Extract and stirred at approximately 30° C. until a suspension was obtained. The pH value was adjusted to approximately 3.5 by adding citric acid.

The wax mixture was heated up to a melting temperature of 75–80° C. and pigment batch 2, the oils, kaolin, talc, boron nitride and the preservatives were stirred in one after the other. Once a substantially homogeneous mass had been obtained, the aforesaid suspension was slowly added while stirring at a temperature of 67–69° C.

Finally, the mixture was stirred at 10000–15000 rpm until it was homogeneous and cooled down to ambient temperature while stirring moderately and at a cooling rate of 1.5° C./min. A powder mass was obtained which is able to be pressed into moulds, which has an excellent colour stability as regards the long-term tanning effect achieved by DHA and Mahakanni and which brings about a very natural brown colour.

EXAMPLE 2

Self-tanning Cream Powder II

| | |
|---|---|
| Ceraflex 3547 | 2 |
| Ozokerite Wax SP 1020 | 2 |
| Candelilla Wax Substitute | 2.5 |
| Synchrowax HGLC | 2.3 |
| Nipasol M | 0.2 |
| Nipagine M | 0.4 |
| α-Tocopherol Acetate | 0.5 |
| Cosmacol EOI | 8 |
| Isopropyl Palmitate | 8 |
| $TiO_2$ | 5 |
| Iron Oxide Red 7054 | 0.4 |
| ZnO | 4 |
| Cogilor Ochre 90076 | 1.5 |
| Black 1557 | 0.14 |
| $SiO_2$ | 4 |
| Crodamol Osu | 7 |
| Modified* Kaolin | 2.5 |
| Orgasol 20002 Extd Nat Cos | 2 |
| Boron Nitride CCS102 | 2 |
| Dryflo Plus | 10 |
| Talc | q.s. ad 100 |
| Silicone Oil | 6 |
| DHA | 2.5 |
| Mahakanni Extract STLC | 3.5 |
| Tulips Extract+ | 2.5 |
| Octyl Methoxycinnamate | 3 |
| Benzophenone-3 | 5.5 |
| Parfum | 0.5 |
| Water | 12 |
| Biophilic H | 3 |

+Tulipa nucleotids, Greentech, St. Beauzire, France
*according to WO96/17588

Processing was done in a similar way as in Example 1. Pigment batch 2 made up 28% by weight. The pH value of the aqueous-alcoholic suspension was 3.8. A powder mass was obtained which is able to be pressed into moulds and which has a very good colour stability and colour intensity although it contains smaller amounts of self-tanning agents.

EXAMPLE 3

Compact Powder

| | |
|---|---|
| Ceraflex 3547 | 1.5 |
| Ozokerite Wax SP 1020 | 0.8 |
| Candelilla Wax Substitute | 0.6 |
| Nipasol M | 0.2 |
| Nipagine M | 0.4 |
| α-Tocopherol Acetate | 0.5 |
| Cosmacol EOI | 1 |
| $TiO_2$ | 5 |
| Iron Oxide Red 7054 | 0.4 |
| ZnO | 0.2 |
| Cogilor Ochre 90076 | 1.5 |
| Black 1557 | 0.14 |
| Modified* Kaolin | 4 |
| Talc | q.s. ad 100 |
| Mahakanni Extract STLC | 2.5 |
| Tulips Extract | 2.5 |
| DHA | 2.5 |
| Parfum | 0.5 |
| Water | 12 |
| Biophilic H | 3 |

*according to WO96/17588

Processing was done as in Example 1. Pigment batch 2 made up 40% by weight. The pH value of the aqueous-alcoholic suspension was 3.3.

What is claimed is:

1. A cosmetic compact or cream powder which comprises a self-tanning agent selected from among mixtures of dihydroxy acetone (DHA) and mahakanni (*Eclipta alba* Hassk) extract and mixtures of DHA, mahakanni extract and tulips extract, additional chromophore pigments, a wax or a mixture of several waxes, a powder base and optionally additional cosmetic auxiliaries and active agents in stable homogeneous distribution, the mahakanni extract being an aqueous extract containing 2-hydroxy-1,4-naphthochinon and eumelanin and the tulips extract being an aqueous extract from tulips exposed to UV radiation containing thymine and pyrimidine dimers and mixtures thereof, wherein the total content of self-tanning agents is in the range of 1–15% by weight relative to the entire composition.

2. A cosmetic compact or cream powder according to claim 1 wherein 2-hydroxy-1,4-naphthochinon is contained in the range of 37–42% by weight and eumelanin is contained in the range of 47–52% by weight relative to the total content of the constituents contained in the extract.

3. A cosmetic compact or cream powder according to claim 1 wherein the self-tanning agent is mixed with a sunscreen.

4. A cosmetic compact or cream powder according to claim 1 wherein the sunscreen is an organic alcohol-soluble sunscreen.

5. A cosmetic compact or cream powder according to claim 3 wherein the sunscreen is contained in the range of 1–10% by weight relative to the entire powder mixture.

6. A cosmetic compact or cream powder according to claim 3 wherein the mixture made up of sunscreen, self-tanning agent and pigments contains pigments in the range of 25–40% by weight relative to the entire powder mixture.

7. A cosmetic compact or cream powder according to claim 1 wherein the water content of the powder does not exceed 15% by weight.

8. A cosmetic compact or cream powder according to claim 1 wherein the total content of self-tanning agents is in the range of 1–15% by weight relative to the entire composition.

9. A cosmetic compact or cream powder according to claim 7 wherein the maximum content of DHA is 5% by weight, the maximum content of mahakanni extract is 10% by weight and the maximum content of tulips extract is 10% by weight.

10. A method for manufacturing the compact or cream powder according to claim 1 which comprises the steps of mixing the powder base and optionally additional cosmetic auxiliaries and active agents and a first portion of 90–50% by weight of the chromophore pigments with the molten wax or wax mixture, subsequently adding the self-tanning agent selected from among mixtures of dihydroxy acetone (DHA) and mahakanni (*Eclipta alba* Hassk) extract and mixtures of DHA, mahakanni extract and tulips extract and a second portion of 10–50% by weight of the pigments in an aqueous-alcoholic suspension having a pH value ranging from 3 to 4 into the molten wax mixture at a temperature of 65–70 C., stirring the entire mixture until it is homogeneous and cooling the mixture while maintaining its homogeneity.

* * * * *